US006758856B2

(12) United States Patent
Saito

(10) Patent No.: US 6,758,856 B2
(45) Date of Patent: *Jul. 6, 2004

(54) CANCER THERMOTHERAPY APPARATUS

(75) Inventor: Yoshiaki Saito, Niigata Pref. (JP)

(73) Assignee: Niigata University, Niigata Pref. (JP)

( * ) Notice: Subject to any disclaimer, the term of this patent is extended or adjusted under 35 U.S.C. 154(b) by 335 days.

This patent is subject to a terminal disclaimer.

(21) Appl. No.: 09/770,840

(22) Filed: Jan. 26, 2001

(65) Prior Publication Data

US 2002/0004674 A1 Jan. 10, 2002

(30) Foreign Application Priority Data

Jul. 4, 2000 (JP) .................................... 2000-201973

(51) Int. Cl.[7] .................................................. A61F 7/00
(52) U.S. Cl. .......................... 607/96; 607/99; 607/100; 607/101; 303/56; 600/410; 600/415
(58) Field of Search ............................. 607/96–102, 90, 607/91; 606/27–33; 330/43–46, 52–57; 600/410, 415

(56) References Cited

U.S. PATENT DOCUMENTS 4,707,668 A * 11/1987 Hoffert ........................ 330/56
5,010,897 A * 4/1991 Leveen ........................ 128/804
5,163,446 A * 11/1992 Saitoh ......................... 128/804

FOREIGN PATENT DOCUMENTS

| JP | 02-036886 | 2/1990 | |
| JP | 05-161717 | 6/1993 | |
| SU | 911661 A | 3/1982 | |
| SU | 1777914 A * | 8/1990 | ............ A61B/5/00 |
| WO | WO 89/07469 | 8/1989 | |

* cited by examiner

Primary Examiner—John Mulcahy
Assistant Examiner—Ahmed M Farah
(74) Attorney, Agent, or Firm—Knobbe Martens Olson & Bear, LLP

(57) ABSTRACT

A cancer thermotherapy apparatus of the present invention has an ortho-hexahedral cavity resonator and a loop antenna on a upper inner wall surface of the cavity resonator. The loop antenna is attached so that its loop face can be parallel to two side inner wall surfaces which are opposed each other, and orthogonal and adjacent to the upper inner wall surface. A high frequency electric power introduced into the cavity resonator is resonated in the parallel direction to the side wall surfaces on an excited mode with a constant electric field intensity along the side wall surfaces. A human body is set in the direction parallel to the side inner wall surfaces in the cavity resonator, and the resonated high frequency electric power is applied to the human body.

12 Claims, 7 Drawing Sheets

(3 of 7 Drawing Sheet(s) Filed in Color)

CANCER THERMOTHERAPY APPARATUS

BACKGROUND OF THE INVENTION (1) Field of the Invention

This invention relates to a cancer thermotherapy apparatus, particularly to a cancer thermotherapy apparatus to set a human body therein and heat a given part of the human body.

(2) Description of the Prior Art

Conventionally, a variety of cancer therapy apparatus have been proposed, but these conventional cancer therapy apparatus can not heat a deep part of a human body effectively.

One of the causes is that in the conventional therapy apparatus, excited modes to maximize their electric field distribution before putting the human body therein at a center of a body axis are employed. Herein, the "body axis" means a line between the head and legs of the human body. That is, if the human body is put in a cavity resonator with such an excited mode to constitute the above therapy apparatus, its predetermined preferable electric field distribution changes, so that a desired deep part of the human body can not be heated sufficiently due to its weak electric field intensity at the deep part thereof.

The other cause is that, although in the conventional therapy apparatus, a high frequency electric power equal to the resonance frequency of the cavity resonator must be applied, the resonance frequency of the cavity resonator becomes indefinite due to the large loss of the cavity resonator as the human body is put in. That is, since the resonant frequency of the cavity resonator can not be measured, the high frequency electric power equal to the resonant frequency can not be applied to the human body, so that the desired deep part of the human body can not be heated effectively by the relatively weak electric field intensity.

SUMMARY OF THE INVENTION

It is an object of the present invention to provide a cancer thermotherapy apparatus capable of heating a desired deep part of the human body effectively and thereby, performing the cancer thermotherapy for the human body effectively.

For achieving the above object, this invention relates to a cancer thermotherapy apparatus comprising an ortho-hexahedral cavity resonator and at least one loop antenna which is attached on an inner wall surface of the cavity resonator so that its loop face can be parallel to two inner wall surfaces of the cavity resonator which are opposed each other, and orthogonal and adjacent to the inner wall surface with the loop antenna.

The cancer thermotherapy apparatus of the present invention resonates, in the ortho-hexahedral cavity resonator, a high frequency electric power introduced into the cavity resonator in the direction parallel to the two inner wall surfaces of the cavity resonator on an excited mode with a constant electric field intensity. The two inner wall surfaces are opposed each other, and are orthogonal and adjacent to the inner wall surface on which the loop antenna is attached. That is, the cancer thermotherapy apparatus of the present invention resonates the introduced high frequency electric power in the direction parallel to the pair of opposed inner wall surfaces of the ortho-hexahedral cavity resonator on the excited mode with the constant electric field intensity. This thermotherapy apparatus mechanism is different from the above conventional one.

Therefore, although the high frequency electric power in the excited mode with the constant electric field intensity is applied to the human body set in the parallel direction in the cavity resonator, it is reflected at one forefront of the human body due to the difference in electric constant between the human body and the interior space of the cavity resonator. The reflected high frequency electric power is reflected again at the other forefront of the human body, and thus, the high frequency electric power is concentrated on a desired part of the human body.

The reflected high frequency electric powers are superposed at the desired part of the human body with time, and thus, the electric field intensity is increased at the desired part. As result, a deep part of the human body can be heated effectively, and the cancer spawned at the deep part can be treated effectively.

Although the above conventional cancer thermotherapy apparatus can have only about 10% complete recovery rate, the cancer thermotherapy apparatus of the present invention can develop the complete recovery rate up to about 50%.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

For better understanding of the present invention, reference is made to the attached drawings, wherein.

DESCRIPTION OF THE PREFERRED EMBODIMENTS

This invention will be described in detail with reference to figures.

Figure 1:
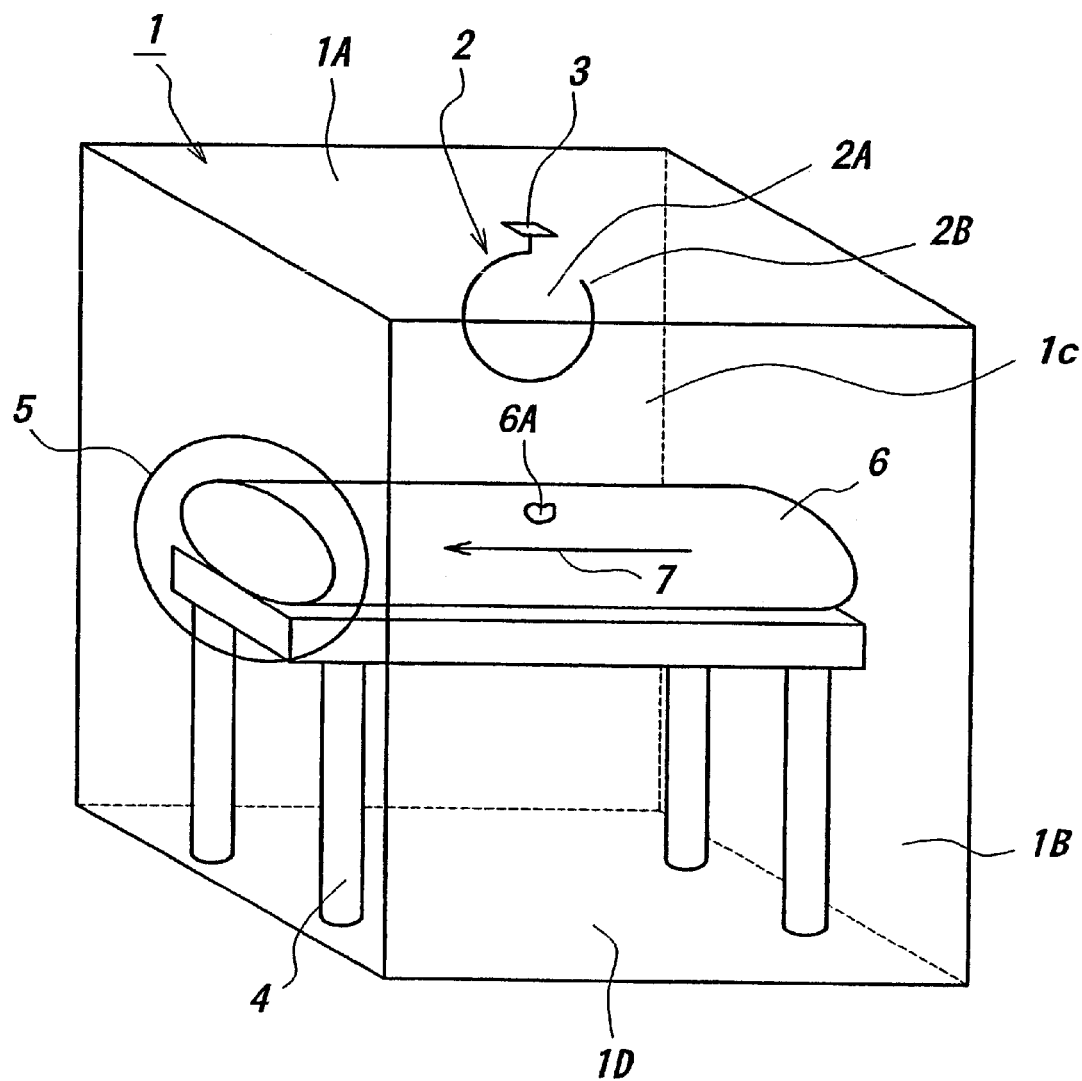
FIG. 1 is a perspective view showing a cancer thermotherapy apparatus according to the present invention.

FIG. 1 is a perspective view showing an embodiment in the cancer thermotherapy apparatus of the present invention. FIG. 1 shows the state in which a human body is put in the cancer thermotherapy apparatus.

The cancer thermotherapy apparatus depicted in FIG. 1 has an ortho-hexahedral cavity resonator 1 and a loop antenna 2 on the upper inner wall surface 1A of the resonator. The loop face 2A of the loop antenna 2 is parallel to the side inner wall surfaces 1B and 1C of the cavity resonator which are opposed each other, and orthogonal and adjacent to the upper inner wall surface 1A on which the loop antenna is provided.

One end of the loop antenna 2 is connected to a connector 3. The connector 3 is connected to an external high frequency electric power supply (not shown) via an impedance matching device (not shown), and thereby, a high frequency electric power is introduced into the cavity resonator 1 from the external high frequency electric power supply. The other end 2B of the loop antenna 2 is opened so as to excite and resonate the introduced high frequency electric power at a given frequency in the cavity resonator 1. Moreover, a table 4 to set the human body 6 on is provided in the cavity resonator 1, and an opening 5 to put the human body 6 in or out of the cavity resonator 1 is formed at the left end thereof. The opening 5 is opened and closed by a given lid as the human body 6 is put in or out of the cavity resonator. During the thermotherapy for the human body, the opening is closed by the lid.

In the cancer thermotherapy using the above apparatus according to the present invention, a given high frequency electric power is introduced into the cavity resonator 1 from the external high frequency electric power supply through the connector 3 before the human body 6 is set in the cavity resonator 1. Then, the introduced high frequency electric power is excited by the loop antenna 2 and resonated at a given frequency in the cavity resonator 1.

In this case, since the loop surface 2A of loop antenna 2 is parallel to the side inner wall surfaces 1B and 1C of the cavity resonator 1, the introduced high frequency electric power is resonated on an excited mode with its constant electric field intensity, that is, on an electric field intensity-unchangeable excited mode along the side inner wall surfaces 1B and 1C of the cavity resonator 1.

Then, the human body 6 is put in the cavity resonator 1 so that its body axis 7 can be parallel to the side inner wall surfaces 1B and 1C of the cavity resonator 1. A new resonated high frequency electric power in the above excited mode is applied to the human body 6.

In this case, the high frequency electric power is reflected at one forefront of the human body 6 due to the difference in electric constant between the human body 6 and the interior space of the cavity resonator 1.

The reflected high frequency electric power is reflected at the other forefront of the human body 6 again, and is concentrated on, for example, a predetermined part of the human body 6A. The reflected high frequency electric powers are superposed at the predetermined part 6A with time and thus, the electric field intensity is increased at the predetermined part 6A. As a result, the predetermined part 6A can be deeply heated effectively and the cancer spawned in the predetermined part can be treated effectively.

Figure 2:
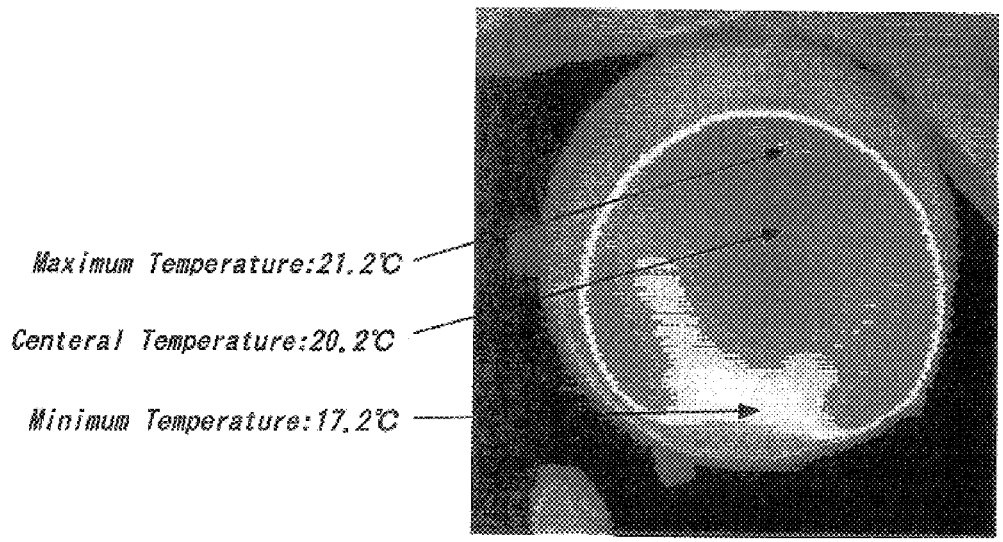
FIG. 2 is a temperature distribution map in a heating experiment using the cancer thermotherapy apparatus shown in FIG. 1.

FIG. 2 is a temperature distribution map in a heating experiment using the apparatus shown in FIG. 1. In this case, a dummy human body composed of TX151 and water was employed instead of a real human body. The heating experiment was carried out for 60 minutes, on condition that the resonant frequency of the cavity resonator was set to 57.7 MHz, and the high frequency electric power was set to 500 W.

As is apparent from FIG. 2, the dummy human body has a maximum temperature of 21.2° C. at its surface part in the side of the loop antenna 2, and has a temperature of 20.2° C. at its inner part. Therefore, the cancer thermotherapy apparatus of the present invention can heat a predetermined part deeply, and thus, the cancer spawn at the predetermined part can be thermally treated effectively.

In the cancer thermotherapy apparatus shown in FIG. 1, however, since the heating effectiveness is decreased as a part of the human body to be heated is away from the loop antenna 2, the nearer part of the human body 6 to the loop antenna 2 is heated effectively and the farther part of the human body 6 may not be heated effectively, so that the farther part may not be heated to a predetermined temperature. It is also apparent from the fact that in FIG. 2, the farther part of the dummy human body is heated to only 17.2° C.

In this case, it is preferable that an additional loop antenna is provided on the lower inner wall surface 1D of the cavity resonator 1 so as to oppose the loop antenna 2. Moreover, the additional loop antenna is provided so that its loop face can be parallel to the loop face 2A of the loop antenna 2 and the side inner wall surfaces 1B and 1C of the cavity resonator 1.

In the case that the additional antenna has the same loop direction as that of the loop antenna 2, respective high frequency electric powers in antiphase are applied to the loop antennas. In the case that the additional antenna has the opposite loop direction to that of the loop antenna 2, respective high frequency electric powers in phase are applied to the loop antennas. Consequently, the heating effectivenesses of these loop antennas are added up, and the human body 6 can be heated effectively in its cross direction.

In this case, the center of the human body in the cross section has a tendency to be heated at the most. Therefore, the center of the human body corresponding to the deepest part thereof can be heated effectively and thus, the cancer spawned at the center can be treated effectively.

Particularly, it is preferable that the additional loop antenna has the opposite loop direction to that of the loop antenna 2 because the above heating effectiveness can be performed only by applying the high frequency electric powers in phase.

Figure 3:
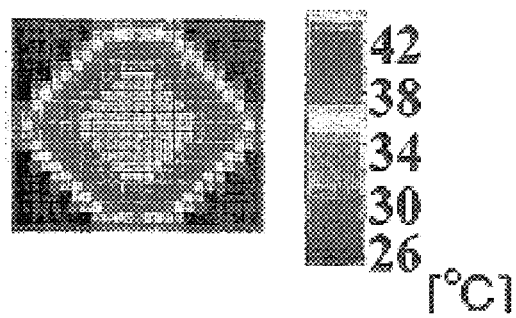
FIG. 3 is a temperature distribution map in a heating simulation using the cancer thermotherapy apparatus shown in FIG. 1.

FIG. 3 is a temperature distribution map in a heating simulation for the human body in the case that the additional loop antenna having the opposite loop direction to that of the loop antenna 2 is provided on the lower inner wall surface 1D of the cavity resonator 1. The heating simulation was carried out for a dummy human body composed of TX151 and water instead of a real human body for 60 minutes, on condition that the resonant frequency of the cavity resonator was set to 57.7 MHz and the high frequency electric power to be introduced was set to 600 W.

As is apparent from FIG. 3, the dummy human body is heated to 40° C. and over entirely in the cross section. Particularly, the center of the dummy human body is heated to 42° C. and over. Therefore, in this preferred embodiment, it is turned out that the human body can be heated uniformly in the cross section, and thus, the center of the human body farthest away from the loop antennas can be heated effectively.

That is, in this preferred embodiment, a predetermined part of the human body can be deeply heated effectively, and thereby, the cancer spawned at the predetermined part can be treated effectively.

Moreover, if three or more loop antennas are provided on some of the inner walls in the cavity resonator so that their loop faces can be parallel to some of the inner wall surfaces of the cavity resonator which are opposed one another, and the respective intensities and phases of high frequency electric powers to be applied to the loop antennas are controlled appropriately, any part of the human body can be heated effectively.

Although the loop antenna can have any length, it is preferable that it has a quarter length of the wavelength of the high frequency electric power to be introduced into the cavity resonator. As a result, the high frequency electric power can be excited effectively and resonated.

Moreover, although the loop face 2A of the loop antenna 2 depicted in FIG. 1 has a substantially circular shape, it has preferably a laterally long elliptical shape or a rectangular shape for heating the human body widely.

Figure 4:
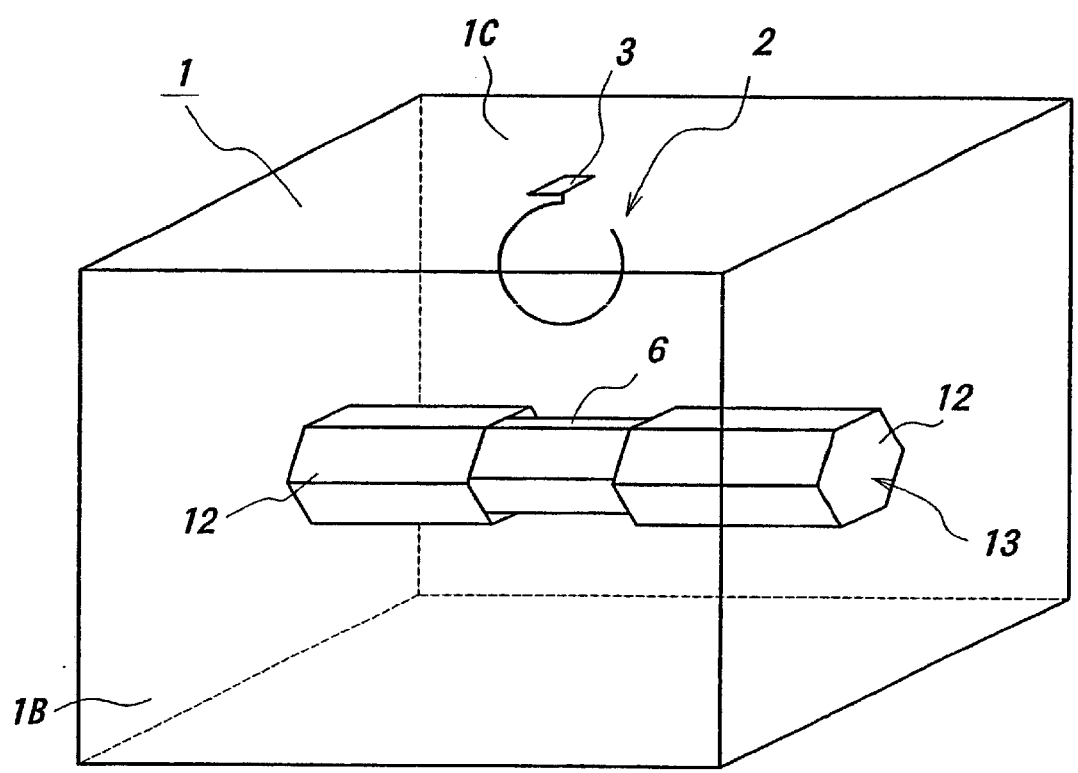
FIG. 4 is a preferred cancer thermotherapy apparatus according to the present invention.

FIG. 4 is a perspective view of another preferred embodiment in the cancer thermotherapy apparatus of the present invention. In FIG. 4, similar parts to the ones in FIG. 1 are designated by the same reference numeral.

In the above cancer thermotherapy apparatus of the present invention, parts of the human body not to be heated such as a head and a foot may be heated. In this case, it is preferable to cover the parts not to be heated with hexahedral tubular metallic members 12 as shown in FIG. 4. Since the above resonated high frequency electric power is not introduced inside the metallic members, the parts covered with the metallic members can not be heated.

Moreover, the bottom surface of one of the metallic members 12 is preferably covered with a metallic plate 13 as shown in FIG. 4. In this case, the high frequency electric power can not be introduced more effectively inside the metallic members 12.

The metallic members 12 can have any shapes including the hexahedral shape shown in FIG. 4 in accordance with the human body shapes.

Figure 5:
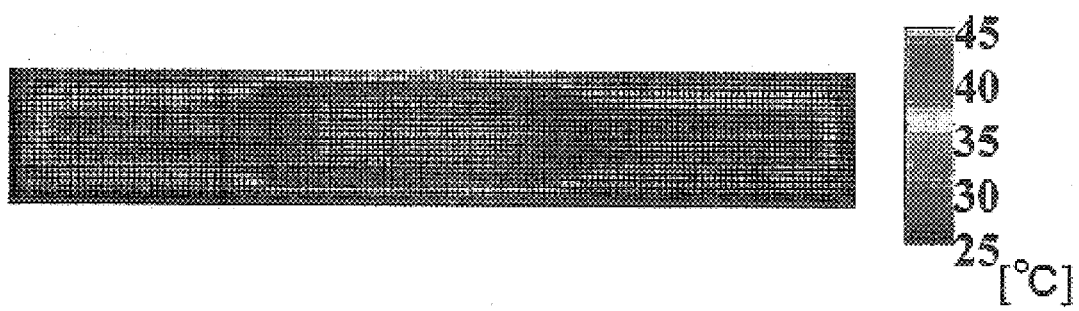
FIG. 5 is a temperature distribution map in a heating simulation using the cancer thermotherapy apparatus shown in FIG. 4.

FIG. 5 is a temperature distribution map in a heating simulation for the human body using the preferred apparatus shown in FIG. 4. The heating simulation was carried out for a dummy human body composed of TX151 and water for 60 minutes, on condition that the resonant frequency of the cavity resonator was set to 57.7 MHz, and the high frequency electric power was set to 300 W. FIG. 5 shows the temperature distribution of the cross section of the dummy human body, taken on the parallel plane to the side inner wall surfaces 1B and 1C of the cavity resonator 1.

As is apparent from FIG. 5, the part of the dummy human body covered with the metallic member 12 is heated to only about 40° C. and below though the part of the human body not covered with the metallic member is heated to a temperature over 40° C. Therefore, it is turned out that the covering using the metallic member can repress the heating of the covered part of the human body effectively.

Figure 6:
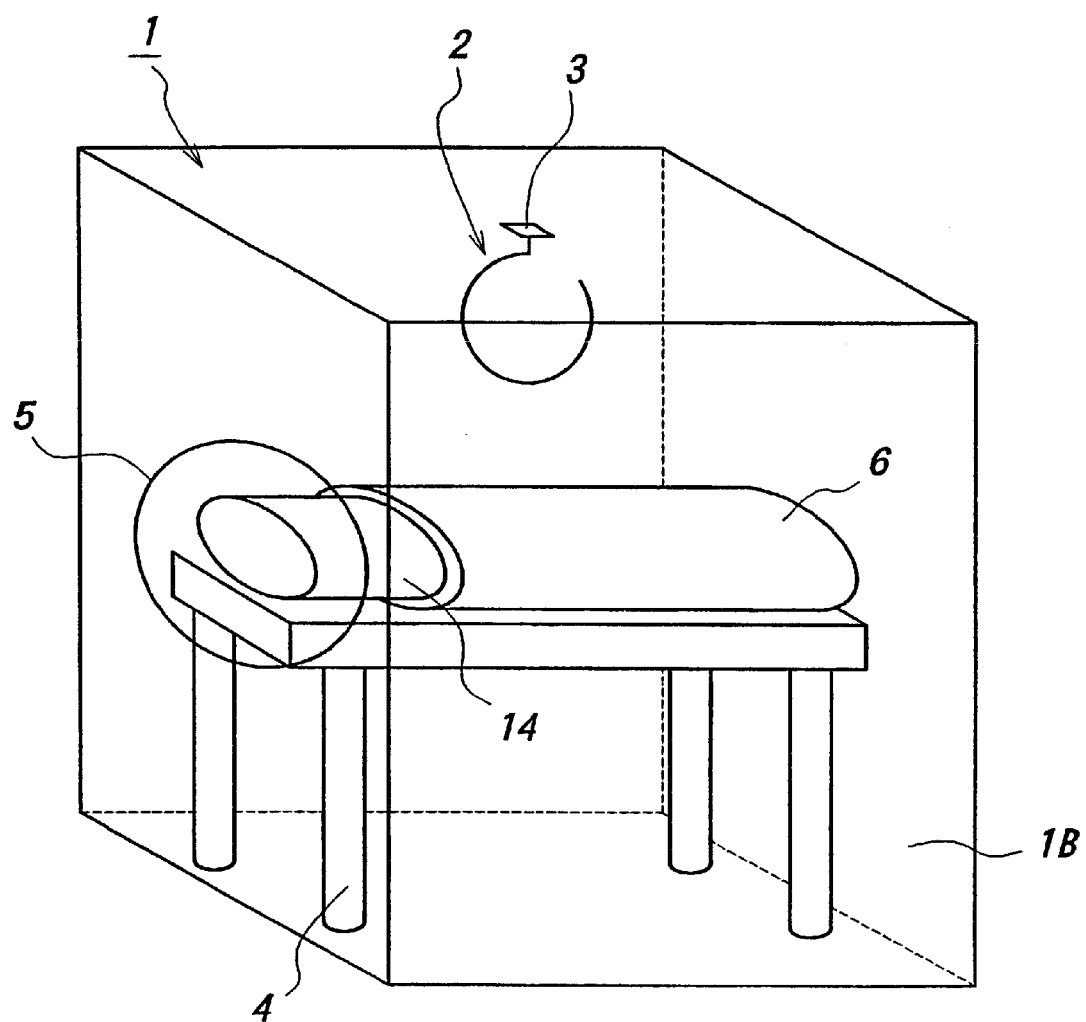
FIG. 6 is another preferred cancer thermotherapy apparatus according to the present invention.

FIG. 6 is a perspective view of still another embodiment in the cancer thermotherapy apparatus of the present invention. In FIG. 6, similar parts to the ones in FIG. 1 are designated by the same reference numerals.

The resonant frequency of the cavity resonator 1 changes in accordance with the size and shape of the human body. However, in view of the frequency dependence in the external high frequency electric power supply, cable length or the impedance matching device, it is desired that the cavity resonator 1 has a constant resonant frequency. Therefore, it is preferable that a resonant frequency controlling member 14 is set at a predetermined position in the cavity resonator 1 as shown in FIG. 6 in order to make constant the resonant frequency thereof.

Concretely, the above constant process is performed by adjusting the size, length, material and position of the resonant frequency controlling member 14. The resonant frequency controlling member 14 may be positioned not only on the table 4 to set the human body on, but also on a pedestal located at a given position in the cavity resonator 1.

The resonant frequency controlling member 14 may be made of a metallic material such as Cu, Al, Fe, a ceramic material, a dielectric material such as Ti and oil, and a human body-equivalent phantom such as TX151, interfacial agent liquid and water. Then, by making the resonant frequency controlling member 14 of the above appropriate material, the resonant frequency of the cavity resonator can be controlled.

In the case of using the hexahedral metallic member as shown in FIG. 4, the resonant frequency of the cavity resonator can be made constant by adjusting the diameter, the length and the position in the resonator of the metallic member.

Figure 7:
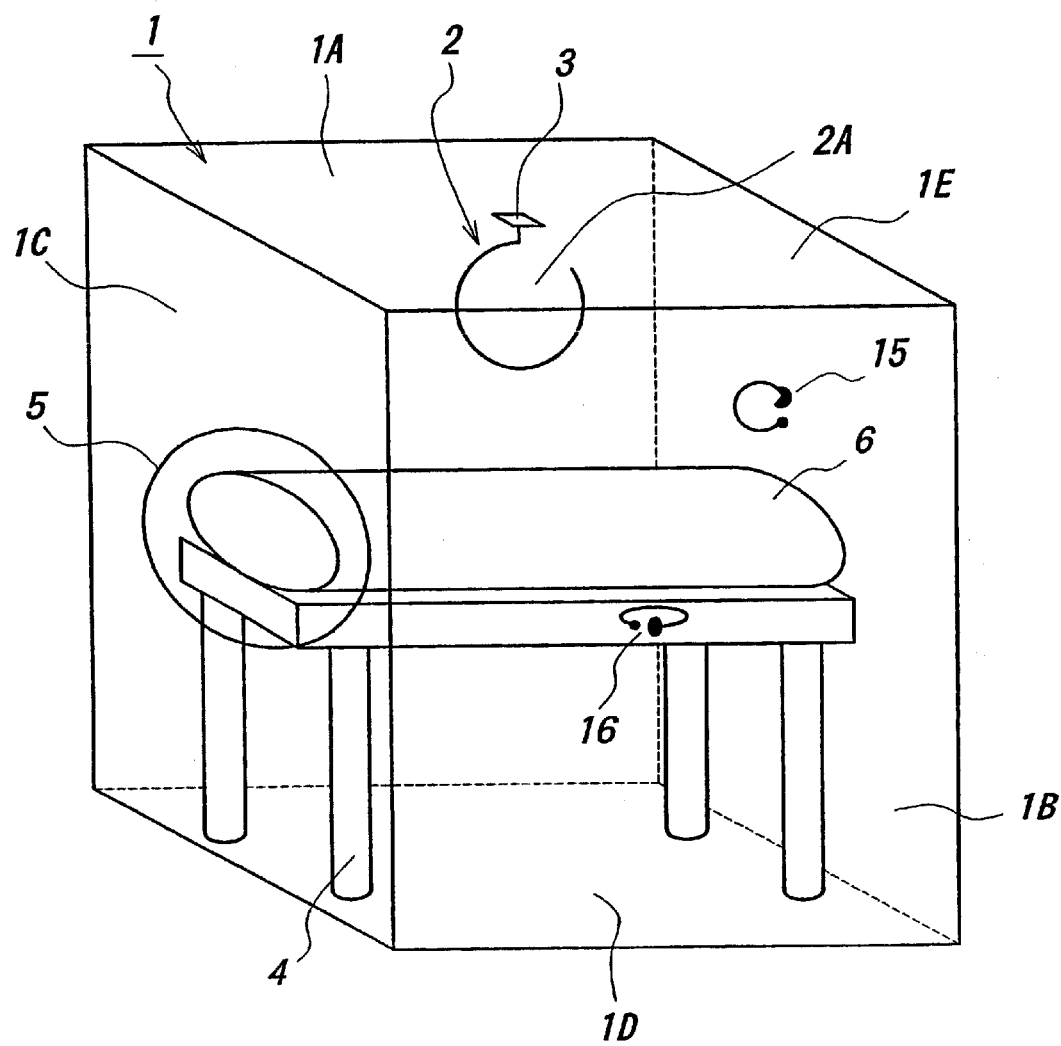
FIG. 7 is still another preferred cancer thermotherapy apparatus according to the present invention.

Next, a measuring method of a resonant frequency in the cancer thermotherapy apparatus of the present invention will be described. FIG. 7 is an explanatory view for the measuring method.

As a predetermined part of the human body is heated effectively according to the cancer thermotherapy apparatus of the present invention, the resonated high frequency electric power is absorbed into the human body largely, resulting in the large degradation of the Q value of the cavity resonator. As a result, the resonant frequency of the cavity resonator can not be measured from its frequency-resonant characteristic by a receiving antenna provided on, for example, the upper inner wall surface 1A on which the loop antenna 2 is set or the lower inner wall surface 1D.

In this case, as shown in FIG. 7, an exciting antenna 15 is provided on the side inner wall surface 1E of the cavity resonator 1 orthogonal to the loop face 2A of the loop antenna 2, and a receiving antenna 16 is provided on the side inner wall surface 1B of the cavity resonator 1 parallel to the loop face 2A. Then, a high frequency electric power is supplied into the cavity resonator 1 from a variable high frequency electric power generator through the exciting antenna 15. In this case, the supplied high frequency electric power is resonated in the cavity resonator 1 without its absorption into the human body 3. Therefore, the high frequency electric power is received at the receiving antenna 16, and thus, the resonant frequency of the cavity resonator 1 can be measured from the frequency of the maximum received signal thereat.

In FIG. 7, the exciting antenna 15 is provided on the side inner wall surface 1E orthogonal to the loop face 2A of the loop antenna 2. However, the exciting antenna 15 may be provided on the side inner wall surface 1B and the receiving antenna 16 may be provided on the side inner wall surface 1E only if the supplied high frequency electric power is resonated in the cavity resonator through its resonant condition. Moreover, the exciting antenna 15 and the receiving antenna 16 may be provided on the side inner wall surface 1E, or on the side inner wall surfaces 1C and 1E orthogonal to the loop face 2A, respectively.

Although the present invention was described in detail with reference to the above example, this invention is not limited to the above disclosure and every kind of variation and modification may be made without departing from the scope of the present invention.

According to the cancer thermotherapy apparatus of the present invention, a given part of a human body can be deeply heated effectively and thus, the cancer thermotherapy can be performed for the human body effectively.

What is claimed is:

1. A cancer thermotherapy apparatus comprising an orthohexahedral cavity resonator and at least one loop antenna which is attached on an inner wall surface of the cavity resonator, wherein a loop face of the loop antenna is parallel to two inner wall surfaces of the cavity resonator which are arranged in a long direction of the cavity resonator, opposed to each other, and orthogonal and adjacent to the inner wall surface with the loop antenna, said cavity resonator being configured to place therein a human body whose longitudinal direction is parallel to the long direction of the cavity resonator.

2. A cancer thermotherapy apparatus as defined in claim 1, wherein two loop antennas are provided on two inner wall surfaces which are opposed each other, respectively, so that their loop faces can be parallel to two inner wall surfaces of the cavity resonator which are opposed each other, and orthogonal and adjacent to each of the inner wall surfaces with the two loop antennas.

3. A cancer thermotherapy apparatus as defined in claim 2, wherein the two loop antennas have their respective opposite loop directions.

4. A cancer thermotherapy apparatus as defined in any one of claims 1–3, wherein the loop antenna has a quarter length of the wavelength of a high frequency electric power to be introduced into the cavity resonator.

5. A cancer thermotherapy apparatus as defined in any one of claims 1–3, wherein the loop antenna has a laterally long elliptical loop face or a rectangular loop face.

6. A cancer thermotherapy apparatus as defined in any one of claims 1–3, further comprising a tubular metallic member to cover a predetermined part of a human body.

7. A cancer thermotherapy apparatus as defined on claim 6, wherein one bottom surface of the tubular metallic member is covered with a metallic plate.

8. A cancer thermotherapy apparatus as defined in any one of claims 1–3, still further comprising a resonant frequency controlling member to control the resonant frequency of the cavity resonator.

9. A cancer thermotherapy apparatus as defined in claim 8, wherein the resonant frequency controlling member is made of a metallic material, a ceramic material or a human body-equivalent phantom.

10. A cancer thermotherapy apparatus as defined in any one of claims 1–3, comprising a pair of an exciting antenna and a receiving antenna to measure the resonant frequency of the cavity resonator.

11. A cancer thermotherapy apparatus as defined in claim 10, wherein at least one of the exciting antenna and the receiving antenna is provided on an inner wall surface of the cavity resonator orthogonal to the loop face of the loop antenna.

12. A cancer thermotherapy apparatus comprising an ortho-hexahedral cavity resonator and plural loop antennas provided on inner wall surfaces of the cavity resonator which are arranged in a long direction of the cavity resonator, said cavity resonator being configured to place therein a human body whose longitudinal direction is parallel to the long direction of the cavity resonator, the plural loop antennas being opposed to one another, loop faces of the plural loop antennas being parallel to the long direction of the cavity resonator, whereby any part of the human body is heated by controlling electric power intensities and phases of the respective high frequency electric powers to the plural loop antennas.

* * * * *